United States Patent
Hashem et al.

(10) Patent No.: US 11,607,449 B2
(45) Date of Patent: Mar. 21, 2023

(54) SYNTHETIC PLASMID DNA VACCINE EXPRESSING A CODON-OPTIMIZED SARS-COV-2 SPIKE PROTEIN

(71) Applicant: KING ABDULAZIZ UNIVERISTY, Jeddah (SA)

(72) Inventors: Anwar M. Hashem, Jeddah (SA); Mohamed A. Alfaleh, Jeddah (SA); Turki S. Abujamel, Jeddah (SA); Sawsan S. Alamri, Jeddah (SA); Abdullah Algaissi, Jeddah (SA); Khalid A. Alluhaybi, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 17/203,116

(22) Filed: Mar. 16, 2021

(65) Prior Publication Data
US 2022/0296700 A1    Sep. 22, 2022

(51) Int. Cl.
| | |
|---|---|
| *A61K 39/215* | (2006.01) |
| *C07K 14/165* | (2006.01) |
| *C12N 15/62* | (2006.01) |
| *C12N 15/85* | (2006.01) |
| *C07K 14/005* | (2006.01) |
| *A61K 39/00* | (2006.01) |

(52) U.S. Cl.
CPC .......... *A61K 39/215* (2013.01); *C07K 14/005* (2013.01); *C07K 14/165* (2013.01); *C12N 15/625* (2013.01); *C12N 15/85* (2013.01); *A61K 2039/53* (2013.01); *A61K 2039/545* (2013.01); *C07K 2319/02* (2013.01); *C12N 2770/20022* (2013.01); *C12N 2770/20034* (2013.01); *C12N 2800/107* (2013.01)

(58) Field of Classification Search
None
See application file for complete search history.

(56) References Cited

U.S. PATENT DOCUMENTS 8,541,003 B2    9/2013    Anderson et al.

OTHER PUBLICATIONS

Silveira et al. (Life Sci. 267(2021) 118919).
Dong et al. (Signal Trans Targ Ther. (2020)5:237).
Muthumani et al. (Sci Transl Med. 2015; 7(301):301).
Zakhartchouk et al. (DNA Cell Biol. 2007; 26(10):721-6).
Wang et al. (J Virol. 2005; 79(3):1906-1910).

*Primary Examiner* — Nicole Kinsey White
(74) *Attorney, Agent, or Firm* — WCF IP

(57) ABSTRACT

A synthetic DNA vaccine against SARS-CoV-2 infection comprises a codon-optimized coding sequence for optimal mammalian expression of a pSARS2 spike glycoprotein (pSARS2-S). The signal peptide may be replaced with the signal peptide from the human IgG2 heavy chain. Systemic S1-specific IgG antibodies and neutralizing antibodies (nAbs) were significantly induced in mice at 2 weeks-post three injections with 100 μg of the pSARS2-S vaccine via intramuscular (IM) needle injection. IM immunization induced Th1-skewed and long-lasting IgG response in BALB/c mice. Immunogenicity and induction of nAbs were enhanced with a needle-free delivery system, wherein two doses were sufficient to elicit significant levels of systemic S1-specific IgG antibodies and nAbs via IM or intradermal immunization.

7 Claims, 8 Drawing Sheets
Specification includes a Sequence Listing.

2A

2B

2C

3A

3B

3C

4A

4B

4C

4D

5A

5B

5C

6A

6B

6C

6D

7A

7B

7C

8A

8B

SYNTHETIC PLASMID DNA VACCINE EXPRESSING A CODON-OPTIMIZED SARS-COV-2 SPIKE PROTEIN

SEQUENCE LISTING

This document incorporates by reference an electronic sequence listing text file, which was electronically submitted along with this document. The text file is named 2021-04-15_15440060AA_seqlisting.txt, is 17 kilobytes, and was created on Apr. 15, 2021.

BACKGROUND OF THE INVENTION

Field of the Invention

The invention generally relates vaccines against the SARS-CoV-2 beta-coronavirus. The invention further relates to a method of inducing an immune response to a codon-optimized SARS-CoV-2 spike protein to protect a subject from acquiring COVID-19.

Background

In December 2019, pneumonia of unknown origin reported in Wuhan, China before it spread globally causing a significant pandemic known as Coronavirus Disease 2019 (COVID-19) pandemic. The causative agent of COVID-19 was identified to be a novel beta-coronavirus (beta-CoV) now known as severe acute respiratory syndrome coronavirus 2 (SARS-CoV-2). Similar to other human coronaviruses, such as the Middle East respiratory syndrome coronavirus MERS-CoV and SARS-CoV, SARS-CoV-2 may have a zoonotic origin. SARS-CoV-2 can infect individuals from different age groups and causes a wide spectrum of disease manifestations. The majority of COVID-19 patients are either asymptomatic or have mild symptoms such as fever, myalgia, and cough. However, some patients may suffer from moderate to severe life-threatening acute respiratory distress syndrome (ARDS) with possible fatal outcomes. The high human-to-human transmission of SARS-CoV-2 poses a significant obstacle toward controlling its spread.

The Coronaviridae family is comprised of enveloped viruses with a positive-sense single-stranded ~30 kb RNA genome. The genome encodes four structural proteins including the surface Spike (S) glycoprotein, the envelope (E) protein, the membrane (M), and the nucleocapsid (N). It also encodes 16 nonstructural proteins (nspl-16) as well as putative and known accessory proteins involved viral replication and pathogenesis. The viral spike (S) protein is capable of inducing a robust immune response. It is comprised of S1 and S2 subunits, with the former known to mediate binding to angiotensin-converting enzyme 2 (ACE2) receptor on host cells and the latter being involved in viral-host membranes fusion. As ACE2 is the main receptor, neutralizing antibodies (nAbs) mainly target the receptor binding domain (RBD) in the S1 subunit. Numerous studies have analyzed antibody responses and found a strong association between the magnitude of anti-S antibody response and patient survival in both MERS-CoV and SARS-CoV, suggesting that viral S protein could represent the main target for vaccine development. This is further supported by the isolation and development of several human nAbs against the SARS-CoV-2 S protein and their ability to neutralize and block viral entry and/or cell-cell spread at very low concentrations, and sometimes to confer prophylactic and therapeutic protection in animal models.

The ideal strategy to rapidly control existing and potential outbreaks of SARS-CoV-2 is to generate a safe and effective vaccine. A drawback of some vaccine platforms, such as protein-based subunit vaccines, is induction of the undesired Th2-skewed response in the case of coronaviruses. For example, see Tseng et al. *PLoS One.* 2012; 7(4); and also Agrawal et al. *Hum Vaccin Immunother.* 2016 September; 12(9):2351-6. Several vaccines candidates based on full-length or truncated S protein are being developed and investigated including DNA vaccines, RNA vaccines, replicating or non-replicating viral vectored vaccines, nanoparticle-based vaccine, whole inactivated MERS-CoV vaccine (WIV), and the S or RBD protein-based subunit vaccines. Many of these vaccines are late clinical trials and/or approved for limited use in different countries.

DNA vaccines against coronaviruses are known in the art. For example, Dong et al. (*Signal Trans Targ Ther.* (2020) 5:237) is a review of SARS-CoV-2 vaccine candidates. The concept and development of nucleic acid vaccines, including DNA vaccines, are described. However, Dong suggests that DNA vaccines may be less effective in inducing nAbs than other vaccine types and that the need for transfer into the nucleus is a disadvantage. Dong teaches a vaccine comprising a codon-optimized SARS-CoV-2 S protein, however this is carried in an adenoviral vector. Epitope design is discussed, but no nucleotide sequences are disclosed. Smith et al (*Nature Com.* 2020; 11:2601) teaches a DNA-based vaccine against consensus sequence encoding a SARS-CoV-2 S protein that neutralized infection in mice and guinea pigs. Muthumani et al. (*Sci Transl Med.* 2015; 7(301):301) teaches codon-optimized anti-spike protein DNA vaccines against MERS coronavirus, including one having an Ig heavy chain ε-1 signal peptide fused to the N terminus of each sequence replacing the N-terminal methionine. The vaccine insert was genetically optimized for improved expression, including codon and RNA optimization. Zakhartchouk et al. (*DNA Cell Biol.* 2007; 26(10):721-6) teaches DNA plasmid vaccines against SARS-CoV-1 spike protein. The four DNA vaccine constructs are four distinct fragments of a codon-optimized SARS-CoV S fused with a leader sequence derived from the human CDS gene. Wang et al. (J Virol. 2005; 79(3):1906-1910) teaches codon-optimized S DNA vaccines and two neutralizing domains on the S protein of SARS-CoV-1. U.S. Pat. No. 8,541,003 to Anderson teaches the use of DNA plasmids that express SARS S protein immunogens, antigens or epitopes as vaccine compositions, wherein a baculovirus signal peptide is used vaccines against SARS-CoV-1.

Despite these advancements, the ongoing global pandemic of COVID-19 requires urgent development of additional prophylactic measures that are safe and effective. There is still a need for additional vaccines that can be rapidly produced and conveniently stored, transported and deployed for mass vaccinations in any climate condition throughout the world.

SUMMARY OF THE INVENTION

The invention is a pharmaceutical composition comprising a vaccine and methods of use to evoke an immune response to the SARS-CoV-2 spike protein and protect an immunized subject from acquiring COVID-19. One embodiment of the invention is a DNA vaccine able to induce an immune response against a SARS-CoV-2 coronavirus, comprising a DNA plasmid encoding a codon-optimized pSARS2 spike glycoprotein (pSARS2-S) as an immunogen from a SARS-CoV-2 coronavirus, wherein the pSARS2-S is codon-optimized for mammalian expression, and wherein the pSARS2-S N-terminal signal peptide is replaced with a signal peptide from a human IgG2 heavy chain.

Another embodiment of the invention is a DNA vaccine able to induce an immune response to a SARS-CoV-2 coronavirus, wherein the immunogen is encoded by nucleotide sequences having the identity of SEQ ID NO:1. The nucleotide sequences of SEQ ID NO:1 encode a protein having the amino acid sequence identity of SEQ ID NO:4.

The DNA sequences encoding the codon-optimized pSARS2-S and encoding the signal peptide from the human IgG2 heavy chain have the nucleotide sequence identity of SEQ ID NO:1. The DNA sequences of the signal peptide from the human IgG2 heavy chain encode an amino acid sequence having the identity of SEQ ID NO:2 and the DNA sequences encoding the signal peptide from the human IgG2 heavy chain have the nucleotide sequence identity of SEQ ID NO:3. Furthermore, the DNA sequences encode a protein having the amino acid identity of SEQ ID NO:4.

Another embodiment of the invention is a method of inducing an immune response to a pSARS2 spike glycoprotein (pSARS2-S) from a SARS-CoV-2 coronavirus in a subject in need thereof, comprising the steps of 1) administering to a subject a dose of a pharmaceutical composition comprising a DNA plasmid encoding a codon-optimized pSARS2 spike glycoprotein (pSARS2-S) from a SARS-CoV-2 coronavirus, wherein the pSARS2-S is codon-optimized for mammalian expression, wherein the pSARS2-S N-terminal signal peptide is replaced with a signal peptide from a human IgG2 heavy chain; 2) allowing a suitable period of time to elapse; and 3) administering at least one additional dose of the pharmaceutical composition.

The pharmaceutical composition comprising the vaccine can be administered intramuscularly or intradermally with a hypodermic, transdermic or intradermal needle or with a needle-free device. In one embodiment, 10 to 150 µg of the DNA plasmid is administered to the subject in each dose. In another embodiment, 25 µg of the DNA plasmid is administered to the subject in each dose. In yet another embodiment, 50 to 100 µg of the DNA plasmid is administered to the subject in each dose.

In another embodiment, the DNA sequences comprising the immunogen of the vaccine have the sequence identity of SEQ ID NO:1, and the invention is a method of inducing an immune response to a pSARS2 spike glycoprotein (pSARS2-S) from a SARS-CoV-2 coronavirus in a subject in need thereof, comprising the steps of 1) administering to a subject a dose of a pharmaceutical composition comprising a DNA plasmid encoding a codon-optimized pSARS2 spike glycoprotein (pSARS2-S) from a SARS-CoV-2 coronavirus, wherein the pSARS2-S is codon-optimized for mammalian expression, wherein the pSARS2-S N-terminal signal peptide is replaced with a signal peptide from a human IgG2 heavy chain; 2) allowing a suitable period of time to elapse; and 3) administering at least one additional dose of the pharmaceutical composition.

Other features and advantages of the present invention will be set forth in the description of invention that follows, and in part will be apparent from the description or may be learned by practice of the invention. The invention will be realized and attained by the compositions and methods particularly pointed out in the written description and claims hereof.

BRIEF DESCRIPTION OF THE DRAWINGS

The accompanying drawings, which are incorporated in and constitute a part of this specification, illustrate embodiments of the invention and, together with a general description of the invention given above and the detailed description given below serve to explain the invention.

FIG. 1A is a schematic diagram of SARS-CoV-2 DNA vaccine construct (pSARS2-S); the SARS-CoV-2 spike gene is indicated by red color. FIG. 1B is an exemplary western blot showing expression of S protein at the expected size from HEK-293A cells transfected with pSARS2-S construct only but not cells only control or cells transfected with empty control plasmid. FIG. 1C immunofluorescent staining of cells transfected with pSARS2-S or empty control plasmid. Transfected cells were stained with anti-SARS-CoV-2 S mouse polyclonal antibodies (green), and nuclei were counterstained with DAPI (blue).

FIG. 2A shows binding of total IgG at 1:100 dilution from each mouse, determined by ELISA at 2, 4 and 8 weeks post first immunization at day 0. FIG. 2B shows end-point titers of total IgG, IgG1, IgG2a and IgG2b, which were determined by ELISA in samples collected on week 8 from immunized mice. FIG. 2C shows IgG2a:IgG1 and IgG2b:IgG ratios, which were calculated from samples collected from immunized mice on week 8. Data are shown as mean±SD for each group from one experiment (n=10). P values were determined by Mann-Whitney test in FIG. 2A and one-way analysis of variance with Bonferroni post-hoc test in FIG. 2B.

FIG. 3A shows binding of total IgG at 1:100 dilution from each, which was determined by ELISA at 2, 4 and 8 weeks post first immunization at day 0. FIG. 3B shows the end-point titers of total IgG, IgG1, IgG2a and IgG2b, which were determined by ELISA in samples collected on week 8 from immunized mice. FIG. 3C shows IgG2a:IgG1 and IgG2b:IgG ratios, which were calculated from samples collected from immunized mice on week 8. Data are shown as mean±SD for each group from one experiment (n=10). P values were determined by Mann-Whitney test in FIG. 3A and one-way analysis of variance with Bonferroni post-hoc test in FIG. 3B.

FIGS. 4A and 4C show the neutralizing activity from serum samples collected from each mouse, and FIGS. 4B and 4D show the IC50 nAb titers. Data are shown as mean±SD in FIGS. 4A and 4C, and bars represent the mean in FIGS. 4B and 4D from one experiment. P values were determined by Mann-Whitney test in 4B and 4D.

FIGS. 6A and 6C show binding of total IgG at 1:100 dilution from each mouse as determined by ELISA at 1, 2, 3 and 4 weeks post first immunization at day 0. FIGS. 6B and 6D show the end-point titer of total IgG as determined by ELISA in samples collected on week 4 from immunized mice. Data are shown as mean±SD in FIGS. 6A and 6C and mean is shown in FIGS. 6B and 6D from an exemplary experiment (n=4-5).

FIG. 8A shows serum samples collected at week 4 post first immunization that were serially diluted and tested in duplicate for their neutralizing activity against rVSV-ΔG/SARS-2-S*-luciferase pseudovirus, as described in Materials and Methods. FIG. 8B shows $IC_{50}$ nAb titers from immunized mice with doses of 25, 50 or 100 µg of pSARS2-S plasmid using either needle injection or needle-free Tropis system. Data are shown as mean±SD from 2 mice from experiment in FIGS. 6 and 7.

DETAILED DESCRIPTION

Figure 1A:
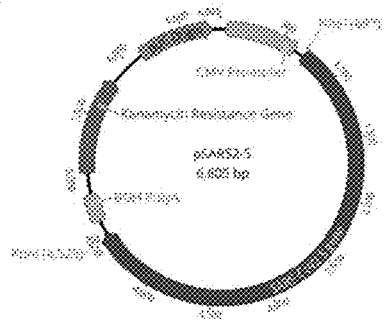
FIGS. 1A-1C shows the design and expression of SARS-CoV-2 Spike protein from DNA vaccine.

The following descriptions and examples illustrate some exemplary embodiments of the disclosed invention in detail. Those of the skill in the art will recognize that there are numerous variations and modifications of this invention that are encompassed by its scope. Accordingly, the description of a certain exemplary embodiment should not be deemed to limit the scope of the present invention.

There is an urgent need to develop a safe and protective vaccine against SARS-CoV-2 to control the COVID-19 pandemic. Synthetic DNA vaccines represent a promising vaccine platform to use in response to outbreaks, such as COVID-19. They can be quickly designed and synthesized based on viral sequences. Their manufacturing is easy and scalable, unlike other platforms such as viral vector or virus-based vaccines. In addition, they are very stable at different storage conditions. Use of consensus S glycoprotein is to induce broad immune response by using conserved sequences covers any possible variation in viral sequences. Therefore, here we analyzed all available SARS-CoV-2 S sequences from GISAID database until Mar. 10, 2020. Such sequence offers protection against broad range of SARS-CoV-2 stains, including emerging strains.

The invention is a pharmaceutical composition comprising a vaccine and methods of use to evoke an immune response to the SARS-CoV-2 spike protein and protect an immunized subject from acquiring COVID-19. In one embodiment, the invention is a DNA vaccine comprises a DNA plasmid encoding a codon-optimized pSARS2 spike glycoprotein (pSARS2-S) as an immunogen from a SARS-CoV-2 coronavirus, wherein the pSARS2-S is codon-optimized for mammalian expression, and wherein the pSARS2-S N-terminal signal peptide is replaced with a signal peptide from a human IgG2 heavy chain.

Another embodiment of the invention is a DNA vaccine comprises an immunogen carried within a plasmid vector. The immunogen is encoded by nucleotide sequences having the identity of SEQ ID NO:1. The nucleotide sequences of SEQ ID NO:1 encode a protein having the amino acid sequence identity of SEQ ID NO:4. A portion of the nucleotide sequences of SEQ ID NO:1 are the nucleotides sequences of SEQ ID NO:3, which encodes the signal peptide from the human IgG2 heavy chain. The nucleotide sequences of SEQ ID NO:3 encode the amino acid sequence of SEQ ID NO:4. In other words, the native signal peptide of the pSARS2-S can be altered or removed and replaced with the amino acid sequences of SEQ ID NO:4.

Another embodiment of the invention is a method of inducing an immune response to a pSARS2 spike glycoprotein (pSARS2-S) from a SARS-CoV-2 coronavirus in a subject in need thereof, comprising the steps of 1) administering to a subject a dose of a pharmaceutical composition comprising a DNA plasmid encoding a codon-optimized pSARS2 spike glycoprotein (pSARS2-S) from a SARS-CoV-2 coronavirus, wherein the pSARS2-S is codon-optimized for mammalian expression, wherein the pSARS2-S N-terminal signal peptide is replaced with a signal peptide from a human IgG2 heavy chain; 2) allowing a suitable period of time to elapse; and 3) administering at least one additional dose of the pharmaceutical composition.

The pharmaceutical composition comprising the vaccine can be administered intramuscularly or intradermally with a hypodermic, transdermic or intradermal needle or with a needle-free device. In one embodiment, 10 to 150 µg of the DNA plasmid is administered to the subject in each dose. In another embodiment, 25 µg of the DNA plasmid is administered to the subject in each dose. In yet another embodiment, 50 to 100 µg of the DNA plasmid is administered to the subject in each dose. The plasmid may be in a circular conformation, or the DNA may be nicked or cleaved by one or more restriction enzymes prior to purification and preparation for administration. The prepared DNA may be suspended in a pharmaceutically acceptable carrier or pH-buffered solution, such as saline or any other physiologically-compatible solution.

In another embodiment, the DNA sequences comprising the immunogen of the vaccine have the sequence identity of SEQ ID NO:1, and the invention is a method of inducing an immune response to a pSARS2 spike glycoprotein (pSARS2-S) from a SARS-CoV-2 coronavirus in a subject in need thereof, comprising the steps of 1) administering to a subject a dose of a pharmaceutical composition comprising a DNA plasmid encoding a codon-optimized pSARS2 spike glycoprotein (pSARS2-S) from a SARS-CoV-2 coronavirus, wherein the pSARS2-S is codon-optimized for mammalian expression, wherein the pSARS2-S N-terminal signal peptide is replaced with a signal peptide from a human IgG2 heavy chain; 2) allowing a suitable period of time to elapse; and 3) administering at least one additional dose of the pharmaceutical composition.

The DNA sequences encoding the codon-optimized pSARS2-S and encoding the signal peptide from the human IgG2 heavy chain have the nucleotide sequence identity of SEQ ID NO:1. The DNA sequences of the signal peptide from the human IgG2 heavy chain encode an amino acid sequence having the identity of SEQ ID NO:2 and the DNA sequences encoding the signal peptide from the human IgG2 heavy chain have the nucleotide sequence identity of SEQ ID NO:3. Furthermore, the DNA sequences encode a protein having the amino acid identity of SEQ ID NO:4.

Synthetic DNA vaccines represent a fast and easy platform to manufacture vaccines compared to other technologies in vaccine development because of their easy design, production in a timely manner, manufacturing scalability and easy and well-established quality control in addition to their temperature stability. In addition, DNA vaccines can elicit Th1-biased immune response, which is a key benefit in mounting an appropriate immune response. The Th1-biased immune response was observed in both BALB/c and C57BL/6J mice. Furthermore, the vaccine of the invention addresses concerns associated with vaccine-induced immunopathology that have been raised for SARS and MERS vaccine candidates. Such immunopathology has been characterized by Th2-skewed immune response and eosinophilia and was reported for different vaccines developed for MERS-CoV and SARS-CoV after viral challenge.

Based on our previous work in developing a vaccine against MERS-CoV as well as other vaccines developed for other coronaviruses, we selected the SARS-CoV-2 S protein as a target because it is a major protein on the surface of the virus and a main target for nAbs (see Hashem et al. *J Infect Diseases.* 2019; 202:1558-67; and Al-Amri et al. *Nature Sci Reports.* 7:44875; DOI:10.1038/srep44875). We developed a DNA-based vaccine as they represent a fast and safe approach to develop vaccines. In vivo testing in mice showed intramuscular immunization with three doses of pSARS2-S via needle injection induced significant and long-lasting levels of Th1-skewed immune response S1-specific IgG in BALB/c and C57BL/6J mice as well as significant levels of nAbs compared to control group with mean $IC_{50}$ titers of $1\times10^3$ in both models. Importantly, needle-free immunization with only two doses of as low as 25 µg of the pSARS2-S via either intramuscular or intradermal routes was able to elicit high levels of S1-specific IgG in a dose-dependent fashion in BALB/c mice. Two doses of 50 µg and 100 µg administered by the needle-free system elicited IgG and nAbs levels that are equivalent or higher than that induced by three doses of 100 µg by needle injection in BALB/c mice. Interestingly, using needle-free system enhanced the immunogenicity of the pSARS2-S vaccine and induced significant levels of S1-specific IgG even at 50 µg and 100 µg when given intradermally albeit the inability of the vaccine to induce any levels of antibodies when administered intradermally via needle injection.

As used historically, the term "antigen" is used to designate an entity that is bound by an antibody, and also to designate the entity that induces the production of the antibody. More current usage limits the meaning of antigen to that entity bound by an antibody, while the term "immunogen" is used for the entity that induces antibody production. Where an entity discussed herein is both immunogenic and antigenic, reference to it as either an immunogen or antigen may be made according to its intended utility. The terms "antigen", "antigenic region" "immunogen" and "epitope" may be used interchangeably herein. As used herein, an antigen, immunogen or epitope is generally a portion of a protein (e.g. a peptide or polypeptide), which has an amino acid sequence that is encoded by a nucleotide sequence.

As used herein, the term "glycoprotein" is used to refer to the protein commonly known as the SARS-CoV-2 spike protein. The spike protein is a glycoprotein and is referred to interchangeably as a protein and a glycoprotein. Furthermore, the sequences encoding the SARS-CoV-2 glycoprotein may also be referred to as a peptide or amino acid sequence.

The invention provides nucleic acid sequences that encode chimeric proteins of the invention. Such nucleic acids include DNA, RNA, and hybrids thereof, and the like. Further, the invention comprehends vectors which contain or house such coding sequences. Examples of suitable vectors include but are not limited to plasmids, cosmids, expression vectors, etc. In a preferred embodiment, the vector will be a plasmid expression vector.

The present invention provides compositions for use in eliciting an immune response. The compositions may be utilized as vaccines to prevent or lessen the severity of COVID-19. By eliciting an immune response, we mean that administration of the immunogen causes the synthesis of specific antibodies and/or cellular proliferation, such as proliferation of immune cells. By "vaccine" we mean a DNA molecule that elicits an immune response which results in protection of an organicism against challenge with SARS-CoV-2. The protective response either wholly or partially prevents or arrests the development of symptoms related to SARS-CoV-2 infection (i.e. the symptoms of COVID-19), in comparison to a non-vaccinated (e.g. adjunct alone) control organisms, in which disease progression is not prevented. The compositions include one or more isolated and substantially purified DNA plasmids or other DNA molecules as described herein, and a pharmacologically suitable carrier. The DNA molecules in the composition may be the same or different, i.e. the composition may be a "cocktail" of different plasmids or molecules, or a composition containing only a single type of plasmid or molecule. The preparation of such compositions for use as vaccines is well known to those of skill in the art. Typically, such compositions are prepared either as liquid solutions or suspensions, however solid forms such as tablets, pills, powders and the like are also contemplated. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. The vaccine preparations of the present invention may further comprise an adjuvant, suitable examples of which include but are not limited to Seppic, Quil A, Alhydrogel, etc. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of DNA in the formulations may vary. However, in general, the amount in the formulations will be from about 0.01-99%, weight/volume.

The methods involve administering a composition comprising the vaccine in a pharmacologically acceptable carrier to a mammal. The mammal may be a human, but this need not always be the case, as veterinary applications of this technology are also contemplated. The vaccine preparations of the present invention may be administered by any of the many suitable means which are well known to those of skill in the art, including but not limited to by injection, inhalation, orally, intranasally, by ingestion of a food product containing the vaccine, etc. In preferred embodiments, the mode of administration is intradermal, subcutaneous or intramuscular. In addition, the compositions may be administered in conjunction with other treatment modalities such as substances that boost the immune system, various antibacterial chemotherapeutic agents, antibiotics, and the like.

The present invention provides methods to elicit an immune response to SARS-CoV-2 and to vaccinate against SARS-CoV-2 infection in mammals. In one embodiment, the mammal is a human However, those of skill in the art will recognize that other mammals exist for which such vaccinations would also be desirable, e.g. the preparations may also be used for veterinary purposes. Examples include but are not limited to companion "pets" such as dogs, cats, etc.; food source, work and recreational animals such as cattle, horses, oxen, sheep, pigs, goats, and the like; or even wild animals that serve as a reservoir of SARS-CoV-2, including but not limited to birds, bats, mice, deer, camelids and others.

Before exemplary embodiments of the present invention are described in greater detail, it is to be understood that this invention is not limited to any particular embodiments described herein and may vary. It is also to be understood that the terminology used herein is for the purpose of describing particular embodiments only, and is not intended to be limiting, since the scope of the present invention will be limited only by the appended claims.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLES

The following Examples provide exemplary compositions comprising nucleotide sequences and methods for inducing an immune response to SARS-CoV-2. The Materials and Methods disclose reagents and assays that are useful in the Examples and embodiments illustrated in FIGS. 1-8. Additional details about the figures can be found in the section entitled "Brief Description of the Drawings".

Materials and Methods

In Silico Design of Codon-Optimized Synthetic Consensus Secreted S Protein

All available SARS-CoV-2 full-length S protein sequences (399 sequences) as of Mar. 10, 2020, were downloaded from GISAID database and dataset was filtered by removing sequences containing ambiguous amino acid codes (BJOUXZ). The final dataset was multiply aligned using CLUSTALW and the Shannon entropy for each amino acid position were determined and the consensus protein sequence was then obtained for the full-length S glycoprotein. The coding sequence for the consensus protein sequence was then codon-optimized for mammalian expression (SEQ ID NO:1) in which the signal peptide (13 amino acid residues) coding sequence from SARS-CoV-2 was replaced with 19 amino acid residues (SEQ ID NO:2) signal peptide coding sequence from the human IgG2 heavy chain (SEQ ID NO:3) at the N-terminus resulting in a codon-optimized synthetic sequence to express secreted consensus full-length S protein (SEQ ID NO:4). Sequences are shown in Table 1.

TABLE 1

Nucleotide sequences used to synthesize a codon-optimized SARS-CoV-2 S construct, and amino acid sequences encoded by the nucleotide sequences.

SEQ ID NO: 1 Codon-optimized consensus synthetic coding sequence for full-length SARS-CoV-2 S protein with human IgG2 heavy chain signal peptide
ATGGGATGGAGCTGTATCATCCTCTTCTTGGTAGCAACAGCTACAGGTGTCCACTCCCA
GTGCGTGAATCTGACTACTCGGACTCAGCTGCCTCCCGCCTATACCAATTCCTTCACCC
GGGGCGTGTACTATCCTGACAAGGTGTTTAGAAGCTCCGTGCTGCACTCTACACAGGA TABLE 1-continued Nucleotide sequences used to synthesize a codon-optimized SARS-CoV-2 S construct, and amino acid sequences encoded by the nucleotide sequences.

```
TCTGTTTCTGCCATTCTTTAGCAACGTGACCTGGTTCCACGCCATCCACGTGAGCGGCA
CCAATGGCACAAAGCGGTTCGACAATCCCGTGCTGCCTTTTAACGATGGCGTGTACTT
CGCCTCTACCGAGAAGAGCAACATCATCAGAGGCTGGATCTTTGGCACCACACTGGAC
TCCAAGACACAGTCTCTGCTGATCGTGAACAATGCCACCAACGTGGTCATCAAGGTGT
GCGAGTTCCAGTTTTGTAATGATCCCTTCCTGGGCGTGTACTATCACAAGAACAATAA
GAGCTGGATGGAGTCCGAGTTTAGAGTGTATTCTAGCGCCAACAATTGCACATTTGAG
TACGTGTCCCAGCCTTTCCTGATGGACCTGGAGGGCAAGCAGGGCAATTTCAAGAACC
TGAGGGAGTTCGTGTTTAAGAATATCGACGGCTACTTCAAAATCTACAGCAAGCACAC
CCCCATCAACCTGGTGCGCGACCTGCCTCAGGGCTTCAGCGCCCTGGAGCCCCTGGTG
GATCTGCCTATCGGCATCAACATCACCCGGTTTCAGACACTGCTGGCCCTGCACAGAA
GCTACCTGACACCCGGCGACTCCTCTAGCGGATGGACCGCAGGAGCTGCCGCCTACTA
TGTGGGCTATCTGCAGCCCCGGACCTTCCTGCTGAAGTACAACGAGAATGGCACCATC
ACAGACGCAGTGGATTGCGCCCTGGACCCCCTGAGCGAGACAAAGTGTACACTGAAG
TCCTTTACCGTGGAGAAGGGCATCTATCAGACATCCAATTTCAGGGTGCAGCCAACCG
AGTCTATCGTGCGCTTTCCTAATATCACAAACCTGTGCCCATTTGGCGAGGTGTTCAAC
GCAACCAGGTTCGCCAGCGTGTACGCATGGAATAGGAAGCGCATCTCTAACTGCGTGG
CCGACTATAGCGTGCTGTACAACTCCGCCTCTTTCAGCACCTTTAAGTGCTATGGCGTG
TCCCCCACAAAGCTGAATGACCTGTGCTTTACCAACGTGTACGCCGATTCTTTCGTGAT
CAGGGGCGACGAGGTGCGCCAGATCGCACCTGGACAGACAGGCAAGATCGCCGACTA
CAATTATAAGCTGCCAGACGATTTCACCGGCTGCGTGATCGCCTGGAACAGCAACAAT
CTGGATTCCAAGGTCGGCGGCAACTACAATTATCTGTACCGGCTGTTTAGAAAGAGCA
ATCTGAAGCCCTTCGAGAGGGACATCTCTACAGAAATCTACCAGGCCGGCAGCACCCC
TTGCAATGGCGTGGAGGGCTTTAACTGTTATTTCCCACTGCAGTCCTACGGCTTCCAGC
CCACAAACGGCGTGGGCTATCAGCCTTACCGCGTGGTGGTGCTGAGCTTTGAGCTGCT
GCACGCACCAGCAACAGTGTGCGGCCCCAAGAAGTCCACCAATCTGGTGAAGAACAA
GTGCGTGAACTTCAACTTCAACGGCCTGACCGGCACAGGCGTGCTGACCGAGTCCAAC
AAGAAGTTCCTGCCATTTCAGCAGTTCGGCAGGGACATCGCAGATACCACAGACGCCG
TGCGCGACCCACAGACCCTGGAGATCCTGGACATCACACCCTGCTCTTTCGGCGGCGT
GAGCGTGATCACACCAGGCACCAATACAAGCAACCAGGTGGCCGTGCTGTATCAGGA
CGTGAATTGTACCGAGGTGCCTGTGGCCATCCACGCCGATCAGCTGACCCCAACATGG
CGGGTGTACAGCACCGGCTCCAACGTGTTCCAGACAAGAGCCGGATGCCTGATCGGAG
CAGAGCACGTGAACAATTCCTATGAGTGCGACATCCCAATCGGCGCCGGCATCTGTGC
CTCTTACCAGACCCAGACAAACTCTCCCAGAAGAGCCCGGAGCGTGGCCTCCCAGTCT
ATCATCGCCTATACCATGTCCCTGGGCGCCGAGAACAGCGTGGCCTACTCTAACAATA
GCATCGCCATCCCAACCAACTTCACAATCTCTGTGACCACAGAGATCCTGCCCGTGTCC
ATGACCAAGACATCTGTGGACTGCACAATGTATATCTGTGGCGATTCTACCGAGTGCA
GCAACCTGCTGCTGCAGTACGGCAGCTTTTGTACCCAGCTGAATAGAGCCCTGACAGG
CATCGCCGTGGAGCAGGATAAGAACACACAGGAGGTGTTCGCCCAGGTGAAGCAAAT
CTACAAGACCCCCCCTATCAAGGACTTTGGCGGCTTCAATTTTTCCCAGATCCTGCCTG
ATCCATCCAAGCCTTCTAAGCGGAGCTTTATCGAGGACCTGCTGTTCAACAAGGTGAC
CCTGGCCGATGCCGGCTTCATCAAGCAGTATGGCGATTGCCTGGGCGACATCGCAGCC
CGGGACCTGATCTGCGCCCAGAAGTTTAATGGCCTGACCGTGCTGCCACCCCTGCTGA
CAGATGAGATGATCGCACAGTACACAAGCGCCCTGCTGGCCGGCACCATCACATCCGG
ATGGACCTTCGGCGCAGGAGCCGCCCTGCAGATCCCCTTTGCCATGCAGATGGCCTAT
AGGTTCAACGGCATCGGCGTGACCCAGAATGTGCTGTACGAGAACCAGAAGCTGATC
GCCAATCAGTTTAACTCCGCCATCGGCAAGATCCAGGACAGCCTGTCCTCTACAGCCT
CCGCCCTGGGCAAGCTGCAGGATGTGGTGAATCAGAACGCCCAGGCCCTGAATACCCT
GGTGAAGCAGCTGAGCAGCAACTTCGGCGCCATCTCTAGCGTGCTGAATGACATCCTG
AGCCGGCTGGACAAGGTGGAGGCAGAGGTGCAGATCGACCGGCTGATCACAGGCAGA
CTGCAGTCTCTGCAGACCTATGTGACACAGCAGCTGATCAGGGCAGCAGAGATCAGGG
CCAGCGCCAATCTGGCAGCAACCAAGATGTCCGAGTGCGTGCTGGGGCCAGTCTAAGAG
AGTGGACTTTTGTGGCAAGGGCTATCACCTGATGTCCTTCCCTCAGTCTGCCCCACACG
GCGTGGTGTTTCTGCACGTGACCTACGTGCCCGCCCAGGAGAAGAACTTCACCACAGC
CCCTGCCATCTGCCACGATGGCAAGGCCCACTTTCCAAGGGAGGGCGTGTTCGTGTCC
AACGGCACCCACTGGTTTGTGACACAGCGCAATTTCTACGAGCCCCAGATCATCACCA
CAGACAATACCTTCGTGAGCGGCAACTGTGACGTGGTCATCGGCATCGTGAACAATAC
CGTGTATGATCCACTGCAGCCCGAGCTGGACAGCTTTAAGGAGGAGCTGGATAAGTAC
TTCAAGAATCACACCTCCCCTGACGTGGATCTGGGCGACATCAGCGGCATCAATGCCT
CCGTGGTGAACATCCAGAAGGAGATCGACCGCCTGAACGAGGTGGCCAAGAATCTGA
ACGAGAGCCTGATCGACCTGCAGGAGCTGGGCAAGTATGAGCAGTACATCAAGTGGC
CCTGGTACATCTGGCTGGGCTTCATCGCCGGCCTGATCGCCATCGTGATGGTGACCATC
ATGCTGTGCTGTATGACATCCTGCTGTTCTTGCCTGAAGGGCTGCTGTAGCTGTGGCTC
CTGCTGTAAATTCGATGAAGATGACTCCGAGCCCGTGCTGAAAGGCGTGAAACTGCAT
TACACTTGA
```

SEQ ID NO: 2 Amino acid sequence of the human IgG2 heavy chain signal peptide
MGWSCIILFLVATATGVHS SEQ ID NO: 3 Coding sequence for the human IgG2 heavy chain signal peptide
ATGGGATGGAGCTGTATCATCCTCTTCTTGGTAGCAACAGCTACAGGTGTCCACTCC TABLE 1-continued Nucleotide sequences used to synthesize a codon-optimized
SARS-CoV-2 S construct, and amino acid sequences encoded by
the nucleotide sequences.

SEQ ID NO: 4 Consensus synthetic SARS-CoV-2 full-length S
protein sequence with human IgG2 heavy chain
signal peptide expressed by codon-optimized
nucleotide sequences MGWSCIILFLVATATGVHSQCVNLTTRTQLPPAYTNSFTRGVYYPDKVFRSSVLHS
TQDLFLPFFSNVTWFHAIHVSGTNGTKRFDNPVLPFNDGVYFASTEKSNIIRGWIFG
TTLDSKTQSLLIVNNATNVVIKVCEFQFCNDPFLGVYYHKNNKSWMESEFRVYSS
ANNCTFENVSQPFLMDLEGKQGNFKNLREFVFKNIDGYFKIYSKHTPINLVRDLPQ
GFSALEPLVDLPIGINITRFQTLLALHRSYLTPGDSSSGWTAGAAAYYVGYLQPRTF
LLKYNENGTITDAVDCALDPLSETKCTLKSFTVEKGIYQTSNFRVQPTESIVRFPNIT
NLCPFGEVFNATRFASVYAWNRKRISNCVADYSVLYNSASFSTFKCYGVSPTKLN
DLCFTNVYADSFVIRGDEVRQIAPGQTGKIADYNYKLPDDFTGCVIAWNSNNLDS
KVGGNYNYLYRLFRKSNLKPFERDISTEIYQAGSTPCNGVEGFNCYFPLQSYGFQP
TNGVGYQPYRVVVLSFELLHAPATVCGPKKSTNLVKNKCVNFNFNGLTGTGVLT
ESNKKFLPFQQFGRDIADTTDAVRDPQTLEILDITPCSFGGVSVITPGTNTSNQVAV
LYQDVNCTEVPVAIHADQLTPTWRVYSTGSNVFQTRAGCLIGAEHVNNSYECDIPI
GAGICASYQTQTNSPRRARSVASQSIIAYTMSLGAENSVAYSNNSIAIPTNFTISVTT
EILPVSMTKTSVDCTMYICGDSTECSNLLLQYGSFCTQLNRALTGIAVEQDKNTQE
VFAQVKQIYKTPPIKDFGGFNFSQILPDPSKPSKRSFIEDLLFNKVTLADAGFIKQYG
DCLGDIAARDLICAQKFNGLTVLPPLLTDEMIAQYTSALLAGTITSGWTFGAGAAL
QIPFAMQMAYRFNGIGVTQNVLYENQKLIANQFNSAIGKIQDSLSSTASALGKLQD
VVNQNAQALNTLVKQLSSNFGAISSVLNDILSRLDKVEAEVQIDRLITGRLQSLQT
YVTQQLIRAAEIRASANLAATKMSECVLGQSKRVDFCGKGYHLMSFPQSAPHGVV
FLHVTYVPAQEKNFTTAPAICHDGKAHFPREGVFVSNGTHWFVTQRNFYEPQIITT
FKEELDKYFKNHTSPDVDLGDISGINDNTFVSGNCDVVIGIVNNTVYDPLQPELDS
ASVVNIQKEIDRLNEVAKNLNESLIDLQELGKYEQYIKWPWYIWLGFIAGLIAIVM
VTIMLCCMTSCCSCLKGCCSCGSCCKFDEDDSEPVLKGVKLHYT DNA Constructs The designed full-length codon-optimized consensus coding sequence for SARS-CoV-2 S gene (SEQ ID NO: 1) was synthesized and cloned into the mammalian expression vector pVAX1 under the control of the cytomegalovirus immediate-early promoter. The resulting plasmid, shown in FIG. 1A, was named pSARS2-S. The coding sequence was cloned between NheI and KpnI restriction sites in the pVAX1 vector using the T4 DNA ligase. The construct was then confirmed by sequencing and restriction digestion analysis. Bulk endotoxin-free preparations of pSARS2-S and the empty pVAX1 plasmid (control) were prepared for animal studies using a plasmid Giga purification kit (Qiagen; Hilden, Germany).

Cells

Baby hamster kidney BHK-21/WI-2 cell line (Kerafast, EH1011) and African green monkey kidney-derived Vero E6 cell line (ATCC, 1586) were cultured in Dulbecco's modified essential medium (DMEM) contained 100 U/ml of penicillin, and 100 µg/ml of streptomycin and supplemented with 5 and 10% fetal bovine serum (FBS) in a 5% $CO_2$ environment at 37° C.

Western Blot 70-90% confluent HEK-293A cells in 6-well plates were transiently transfected with 2 µg of pSARS2-S or empty control plasmid (pVAX1) using JetPRIME® Transient Transfection Protocol and Reagents (Polyplus-Transfection SA; New York) according to manufacturer's instructions. Transfected cells were incubated at 37° C. in a 5% $CO_2$ incubator for 48 h. Transfected cells were then washed with phosphate-buffered saline (PBS) and lysed with radioimmunoprecipitation assay buffer (RIPA buffer) (Sigma-Aldrich; St. Louis, Mo.). The lysates were subjected to western blot analysis for protein expression using mouse anti-S (SARS-CoV-2) polyclonal antibodies.

Immunofluorescence Analysis.

HEK-293A cells were seeded on an 8-well cell culture slide [growth area/well ($cm^2$): 0.98 and working volume/well (ml): 0.20-0.60] to be 70% confluent by the next day and incubate at 37° C., 5% $CO_2$. The next day, cells were transfected with 0.2 µg of pSARS2-S or empty control plasmids using JetPRIME® Transient Transfection Protocol and Reagents (Polyplus) according to manufacturer's instructions, followed by incubation at 37° C. in a 5% $CO_2$ incubator for 24 h. The media was removed, and then cells were washed with PBS and fixed with 4% formaldehyde at 4° C. for 10 min. Cells were washed twice with PBS and permeabilized with 0.2% PBS-T (Triton 100) at 4° C. for 20 min. Cells were then washed twice with PBS-T. Wells were blocked with blocking buffer (2% goat serum in PBS-T) at room temperature for 30 min and washed twice with PBS-T. Cells were then incubated with mouse anti-SARS-CoV-2 S polyclonal antibodies in blocking buffer at 1:1000 dilution at 4° C. for 1 h. After three washes with PBS-T, Alexa Fluor-488 labeled goat anti-mouse IgG H&L secondary antibody at 1:500 dilution in blocking buffer and incubated in the dark at room temperature for 1 h. Cells were washed again for three times with PBS-T, and slides were mounted with VECTASHIELD® antifade mounting medium with DAPI counter stain (Vector Laboratories; Burlingame, Calif.). Images were captured using Olympus BX51 Fluorescence Microscope.

Animal Studies.

Six to 8-week-old female BALB/c or C57BL/6J mice were obtained from and housed in the animal facility in King Fand Medical Research Center (KFMRC), King Abdulaziz University (KAU), Jeddah, Saudi Arabia. All animal experiments were conducted in accordance with the guidelines and approval of the Animal Care and Use Committee (ACUC) at KFMRC and ethical approval (04-CEGMR-Bioeth-2020). In one experiment, two groups of BALB/c or C57BL/6J mice (10 per group) were intramuscularly immunized via needle injection with 3 doses of 100 µg of either pSARS2-S or control plasmid at 2 weeks interval and blood samples were collected for serological testing every 2 weeks starting from day 0 pre-bleed until week 8. In another experiment, three groups of BALB/c mice (5 per group) were immunized intramuscularly, intradermally or subcutaneously via needle injection with 3 doses of 100 μg of either pSARS2-S or control plasmid at 2 weeks interval and blood samples were collected every 2 weeks until week 17 post primary immunization. In a third experiment, BALB/c mice (4-5 per group) were intramuscularly or intradermally immunized with 2 doses of 25 μg, 50 μg or 100 μg of pSARS2-S plasmid at 2 weeks interval using either needle injection or needle-free Tropis system (PharmaJet; Golden, Colo.) and blood samples were collected every week until week 4 post primary immunization.

Indirect ELISA.

The end-point titers or optical density (OD) readings at 1:100 dilution of total anti-S1 IgG or its isotypes (IgG1, IgG2a and IgG2b) from immunized mice were determined by enzyme-linked immunosorbent assay as described previously (ELISA) as previously described (Al-Amri et al. *Sci Rep.* 2017 Mar. 23; 7:44875). Briefly, 96-well EU Immulon 2 HB plates (Thermo Fisher Scientific; Waltham, Mass.) were coated overnight at 4° C. with the SARS-CoV-2 S1 subunit (amino acids 1-685) (Sino Biological; China) at 0.5 μg/ml in PBS (50 ul/well). Then, the plates were washed three times with washing buffer (PBS containing 0.1% Tween-20 (PBS-T)). This was followed by blocking with 200 ul/well of blocking buffer (5% skim milk in PBS-T) for 1 h at room temperature. Plates were washed three times and incubated with a 2-fold serial dilution of mouse sera (100 ul/well) starting from 1:100 dilution in blocking buffer and incubated for 1 h at 37° C. Some samples collected at different time points were only tested at 1:100 dilution. After three washes, peroxidase-conjugated rabbit anti-mouse IgG secondary antibodies as well as anti-IgG1, IgG2a or IgG2b antibodies (Jackson Immunoresearch Laboratories; West Grove, Pa.) were added at dilutions recommended by the manufacturer and incubated for 1 h at 37° C. as 100 ul/well. Excess secondary antibodies were removed by three washes and color was developed by adding 3,3',5,5'-tetramethylbenzidine (TMB) substrate (KPL, Gaithersburg, Md.) for 30 min. Finally, reactions were stopped with 0.16 M sulfuric acid and absorbance was read spectrophotometrically at 450 nm using the ELx808™ Absorbance Microplate Reader (BioTek; Winooski, Vt.). End-point titers were determined and expressed as the reciprocals of the highest dilution with OD reading above the cut-off value defined as the mean of the control group plus three standard deviations (SD).

SARS-CoV-2 Pseudovirus Neutralization Assay.

Pseudovirus microneutralization assay was performed as previously described (Almahboub et al. *Front Microbiol.* 2020 Sep. 4; 11:2020). Briefly, rVSV-ΔG/SARS-2-S*-luciferase pseudovirus was generated by transfecting BHK21/WI-2 cells with 46 μg of pcDNA expressing codon-optimized full-length SARS-CoV-2 S protein (GenBank accession number: MN908947) using Lipofectamine™ 2000 transfection reagent (Invitrogen; Carlsbad, Calif.). 24 h later, transfected cells were infected with rVSV-ΔG/G*-luciferase at a multiplicity of infection (moi) of 4 and the supernatant containing the generated rVSV-ΔG/SARS-2-S*-luciferase pseudovirus was collected 24 h post-infection. The collected virus was titrated by measuring luciferase activity from serially diluted supernatant on Vero E6 cells and the titer was expressed as a relative luciferase unit (RLU). Neutralization assay was then conducted by incubating two-fold serial dilutions of heat-inactivated mouse sera from vaccinated and control groups starting at a 1:20 dilution (in duplicate) with DMEM were incubated with DMEM-5 containing $5 \times 10^4$ RLU rVSV-ΔG/SARS-2-S*-luciferase pseudovirus for 1 h at 37° C. in a 5% $CO_2$ incubator. Pseudovirus-serum mixtures were transferred onto confluent Vero E6 cell monolayers in white 96-well plates and incubated for 24 h at 37° C. in a 5% $CO_2$ incubator. 24 h later, cells were lysed, and luciferase activity was measured using Luciferase Assay System (Promega; Madison, Wiss.) according to the manufacturer's instructions, and the luminescence was measured using a Biotek Synergy microplate luminometer (BioTek Instruments; Winooski, Vt.). Cell-only control (CC) and virus control (VC) were included with each assay run. The median inhibitory concentration ($IC_{50}$) of neutralizing antibodies (nAbs) was determined using four-parameter logistic (4PL) curve in GraphPad Prism V8 software (GraphPad Software; San Diego, Calif.) and calculated as the reciprocal of the serum dilution at which RLU were reduced by 50% compared with the virus control wells after subtraction of the background RLUs in the control groups with cells only.

Statistical Analysis

Statistical analyses and graphical presentations were conducted with the GraphPad Prism V8 software. Statistical analysis was conducted using one-way analysis of variance with Bonferroni post-hoc test to adjust for multiple comparisons between groups, or Mann-Whitney test. All values are depicted as mean±SD and statistical significance is reported as *, $P \leq 0.05$ and **, $P \leq 0.01$.

Example 1

In Vitro Protein Expression From the Synthetic DNA Vaccine

Figure 1B:
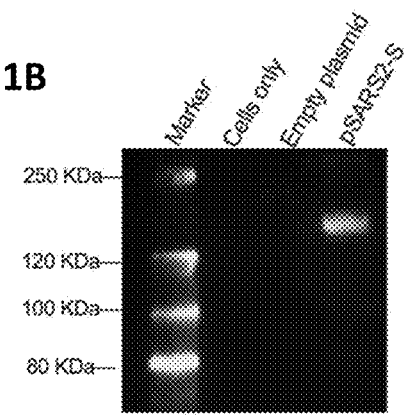
Figure 1C:
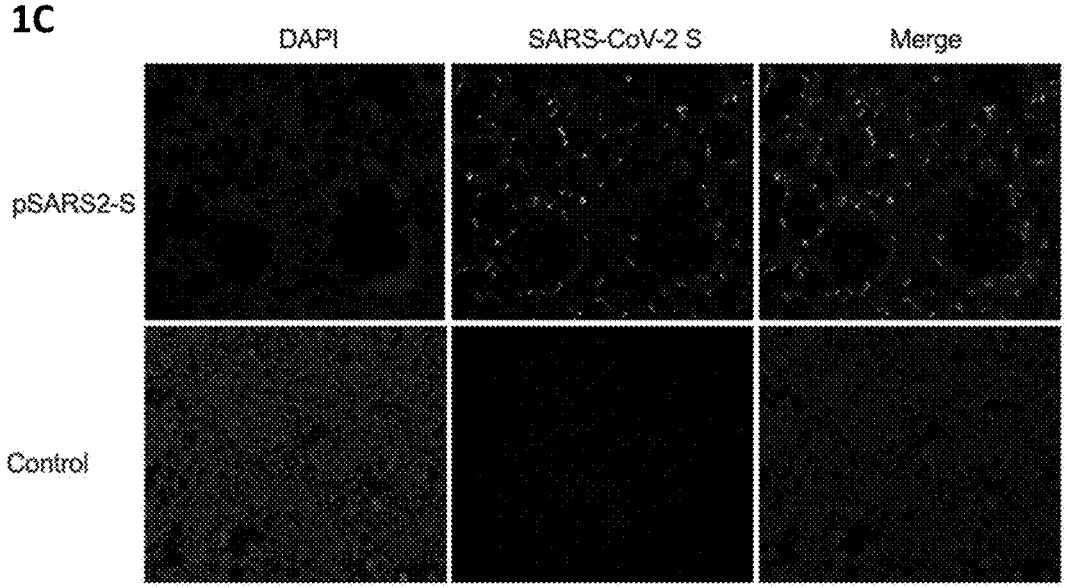

Prior to animal experiments, protein expression from the DNA construct was confirmed in vitro in HEK-293A cells. Western blot analysis confirmed that the recombinant construct was able to express the spike protein indicated by the band observed at expected molecular weight, as shown in FIG. 1B. Immunofluorescence analysis was performed to visualize the expression of SARS-CoV-2 Spike protein in transfected HEK-293A cells. As shown in FIG. 1C, the S protein expression was only detected in cells transfected with pSARS2-S using mouse anti-SARS-CoV-2 S polyclonal antibodies but not in cells transfected with the control plasmid.

Example 2

Figure 2A:
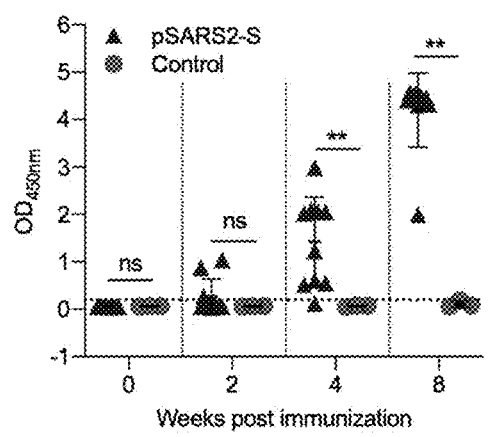
FIGS. 2A-2C show the antibody response against SARS-CoV-2 S1 in BALB/c mice. Mice were intramuscularly immunized with 3 doses of 100 µg each at 2 weeks interval using either pSARS2-S or control plasmid.
Figure 2B:
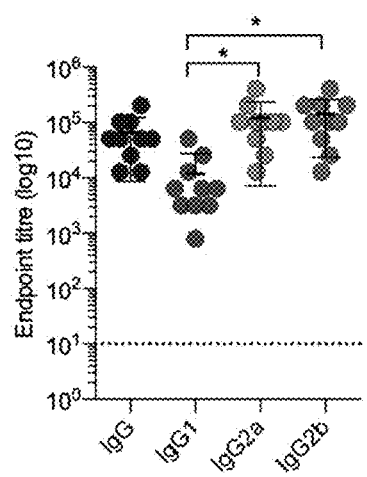
Figure 2C:
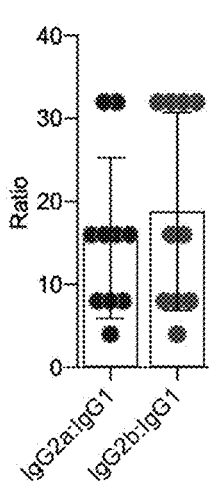
Figure 3A:
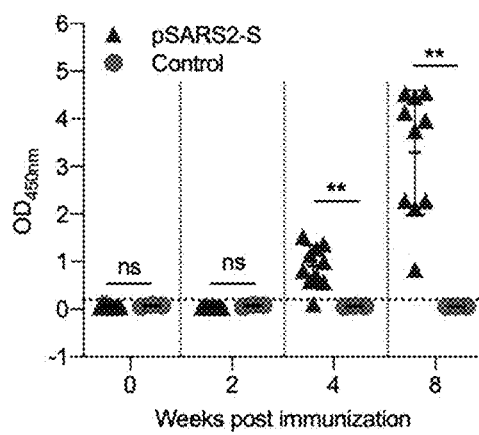
FIGS. 3A-3C show the antibody response against SARS-CoV-2 S1 in C57BL/6J mice. Mice were intramuscularly immunized with 3 doses of 100 µg each at 2 weeks interval using either pSARS2-S or control plasmid.
Figure 3B:
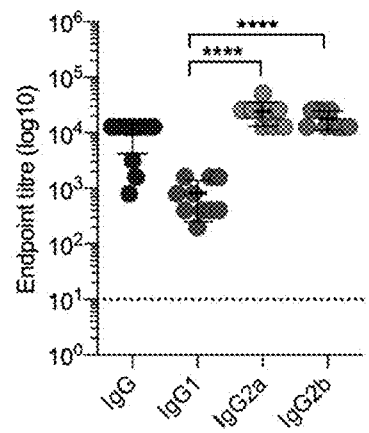
Figure 3C:
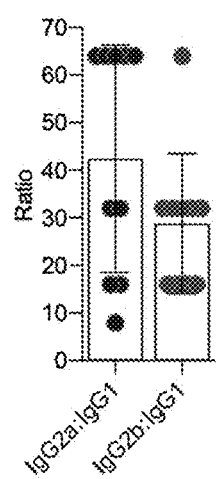
Figure 4A:
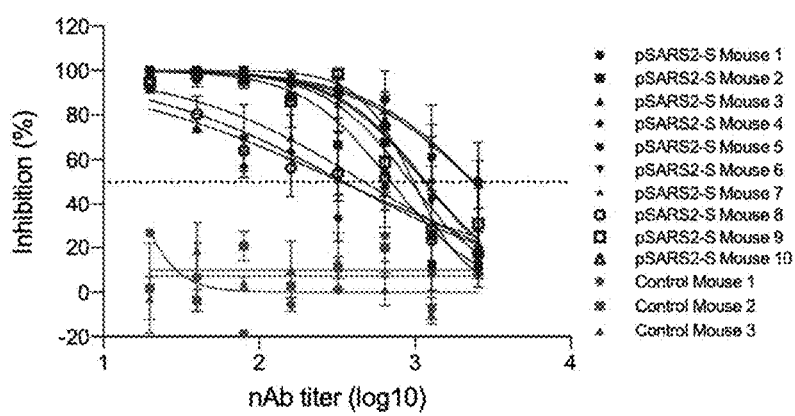
FIGS. 4A-4D show the neutralizing antibody (nAb) response after intramuscular immunization in BALB/c and C57BL/6J mice. BALB/c mice (shown in FIGS. 4A and 4B) or C57BL/6J mice (shown in FIGS. 4C and 4D) were immunized with 3 doses of 100 µg each at 2 weeks interval using either pSARS2-S (n=10) or control plasmid (n=3). Serum samples were collected at week 8 post first immunization and serially diluted and tested in duplicate for their neutralizing activity against rVSV-ΔG/SARS-2-S*-luciferase pseudovirus as described in Materials and Methods.
Figure 4B:
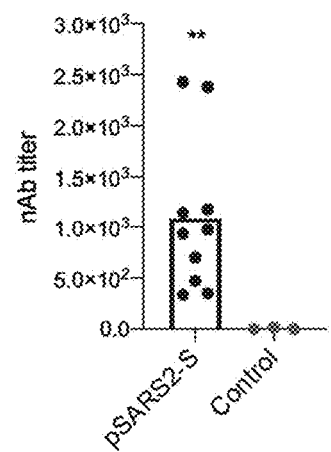
Figure 4C:
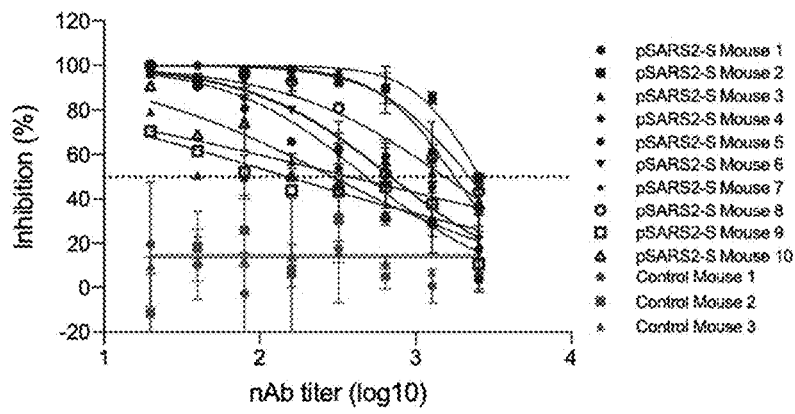
Figure 4D:
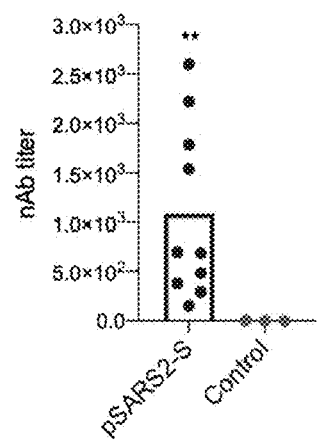
Figure 5A:
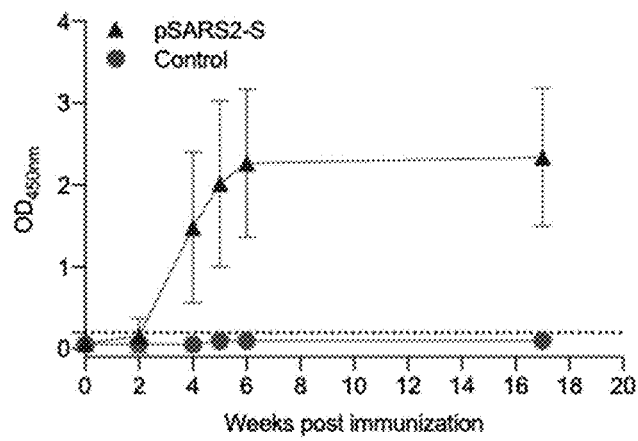
FIGS. 5A-5C show the long-term IgG response in mice immunized with different routes. BALB/c mice were immunized with 3 doses of 100 µg each at 2 weeks interval using either pSARS2-S or control plasmid via (5A) intramuscular, (5B) intradermal, or (5C) subcutaneous routes. S1-binding total IgG from each mouse was determined by ELISA at 1:100 dilution at 2, 4 and 8 weeks post first immunization at day 0. Data are shown as mean±SD for each group from one experiment (n=5).
Figure 5B:
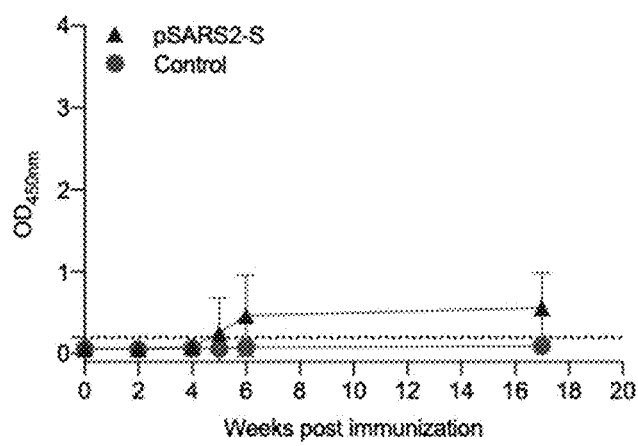
Figure 5C:
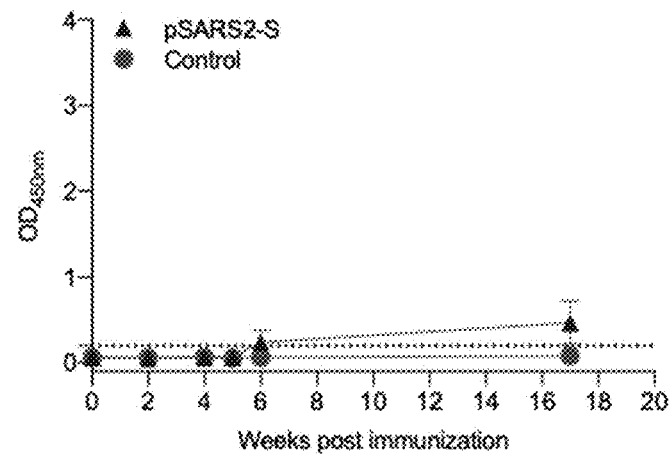
Figure 6A:
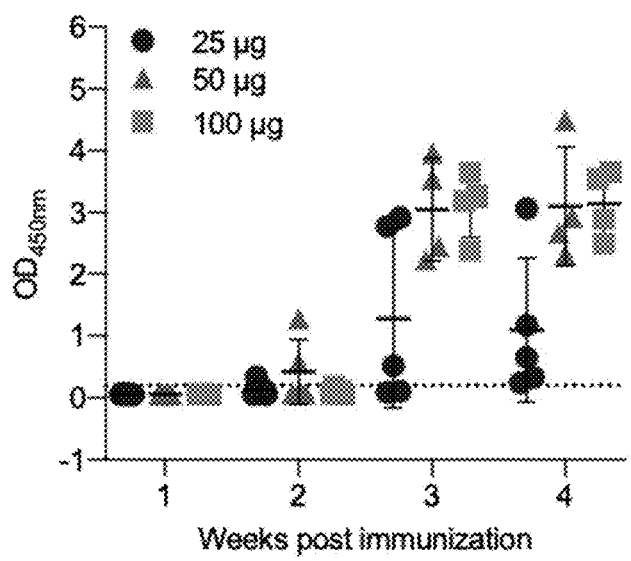
FIGS. 6A-6D show the antibody response against SARS-CoV-2 S1 in BALB/c mice immunized with needle-free Tropis system. Mice were immunized either (6A and 6B) intramuscularly or (6C and 6C) intradermally with 2 doses of 25, 50 or 100 µg at 2 weeks interval using pSARS2-S plasmid.
Figure 6B:
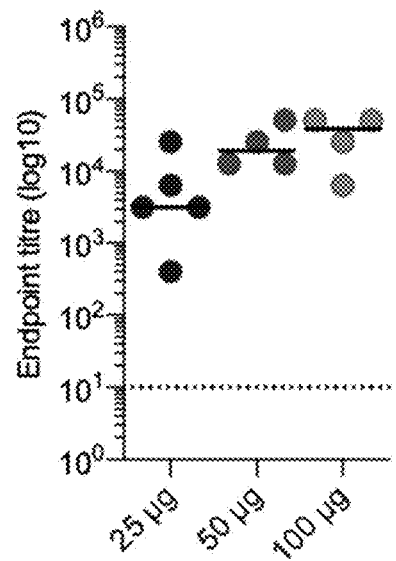
Figure 6C:
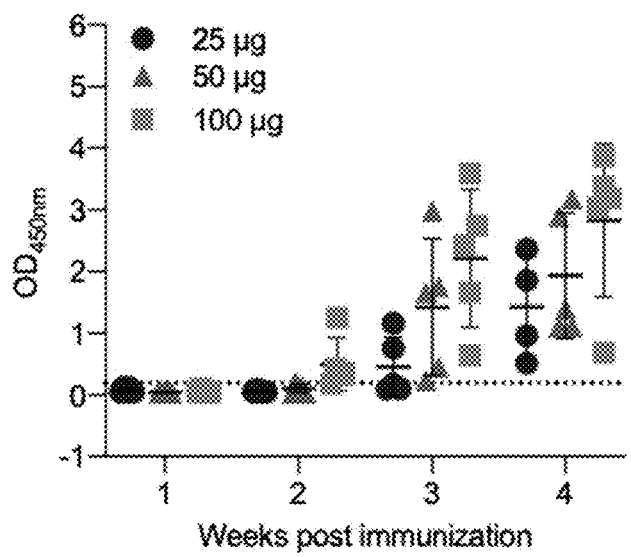
Figure 6D:
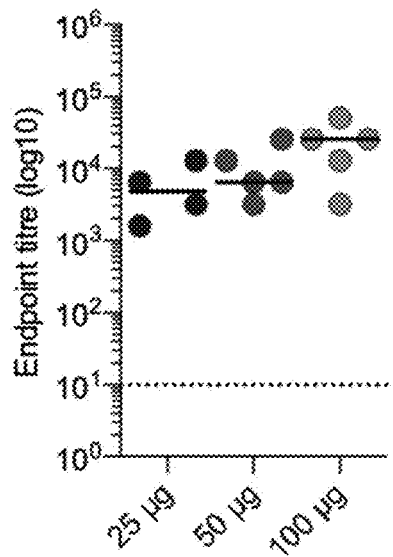
Figure 7A:
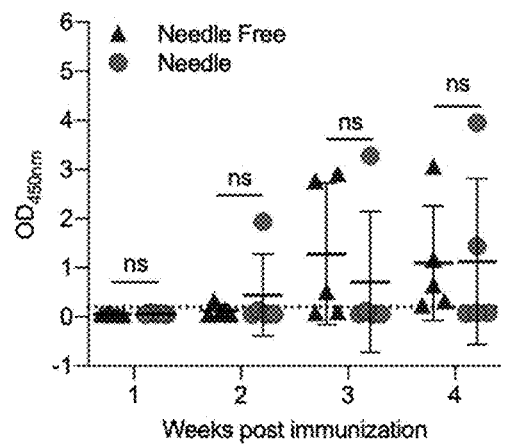
FIGS. 7A-7C show the antibody response against SARS-CoV-2 S1 in BALB/c mice immunized using either needle injection or needle-free Tropis system. BALB/c mice were immunized with 2 doses of (7A) 25, (7B) 50 or (7C) 100 µg of pSARS2-S plasmid at 2 weeks interval using either needle injection or needle-free Tropis system. Binding of total IgG at 1:100 dilution from each mouse was determined by ELISA at 1, 2, 3 and 4 weeks post first immunization at day 0. Data are shown as mean±SD from 4-5 mice from experiment in FIG. 6. P values were determined by Mann-Whitney test.
Figure 7B:
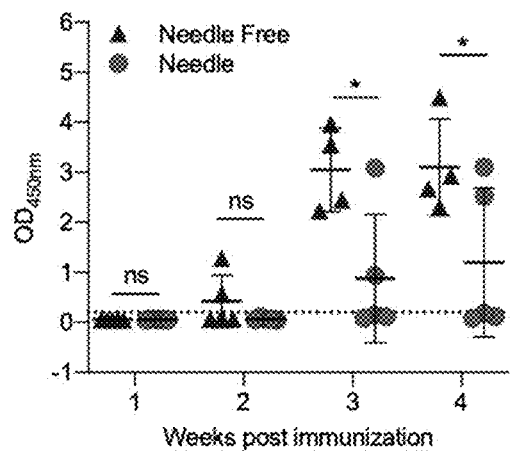
Figure 7C:
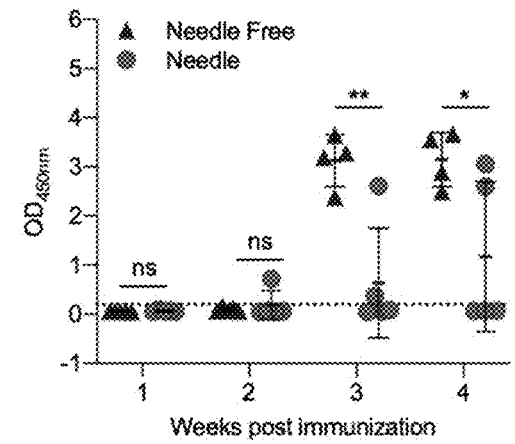
Figure 8A:
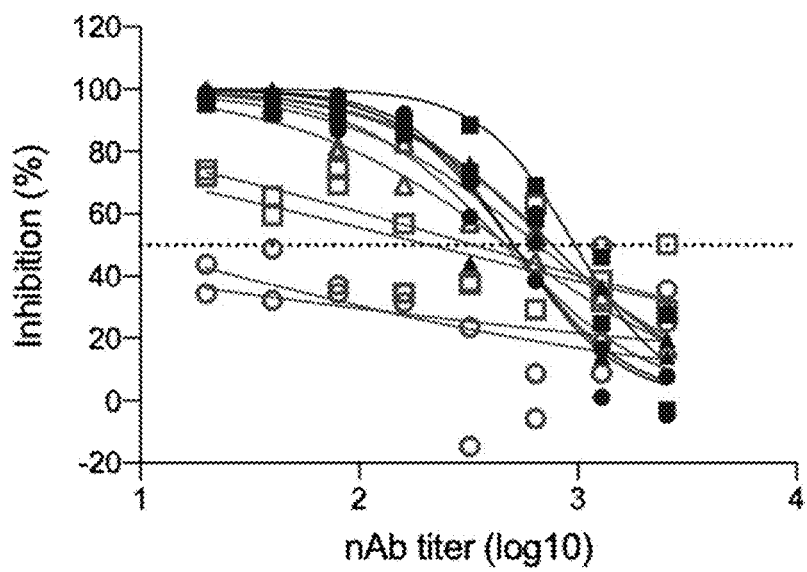
FIGS. 8A and 8B show the neutralizing antibody response after intramuscular immunization in BALB/c using either needle injection or needle-free Tropis system. BALB/c mice were immunized with 2 doses of 25, 50 or 100 µg of pSARS2-S plasmid at 2 weeks interval using either needle injection or needle-free Tropis system.
Figure 8B:
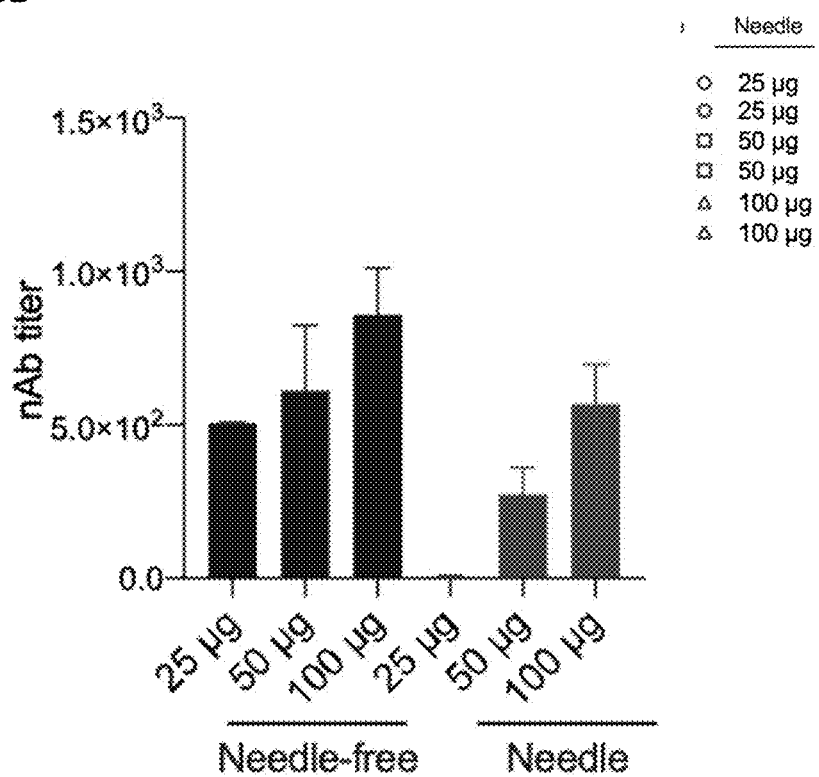

Intramuscular Immunization With the Synthetic DNA Vaccine Elicits Significant and Long Lasting Th1-Skewed Humoral Immune Response in Mice The immunogenicity of the generated naked DNA vaccine candidate was evaluated in BALB/c and C57BL/6J mice. Mice intramuscularly immunized with three doses of the vaccine induced significant levels of S1-specific IgG. Specifically, while two doses elicited significant levels of S1-specific IgG in both BALB/c and C57BL/6J mice, samples collected 2 weeks post-third immunization (i.e. on week 8) showed higher significant levels compared to control groups immunized with the control plasmid (FIGS. 2A and 3A). Immunization with pSARS2-S significantly induced higher levels of S1-specific IgG2a and IgG2b compared to IgG1 in both animal models (FIGS. 2B and 3B), demonstrating a Th1-skewed immune response as shown by the high IgG2a/IgG1 or IgG2b/IgG1 ratios (FIGS. 2C and 3C).

To further investigate the ability of the developed vaccine to elicit nAbs, sera from immunized and control mice were tested in pseudovirus microneutralization assay. As shown in FIG. 4, sera collected on week 8 from pSARS2-S immunized group induced significant levels of nAbs compared to control group with mean $IC_{50}$ titers of $1\times10^3$ in both BALB/c and C57BL/6J mice. As expected, no neutralizing activity was observed from mice immunized with control plasmid. Interestingly, intradermal and subcutaneous immunization of BALB/c mice with three doses of pSARS2-S failed to induce any significant IgG levels (FIG. 5). On the other hand, such immunization via intramuscular route elicited long-lasting S1-specific IgG that lasted until week 17 post-primary immunization. These data demonstrate that intramuscular immunization with this synthetic codon-optimized DNA vaccine induced nAbs and long-lasting Th1-skewed antibody response in mice.

Example 3

Needle Free Injection Enhances the Immunogenicity of the Synthetic DNA Vaccine in Mice To further improve the immunogenicity of the naked synthetic DNA vaccine, a needle-free Tropis system was used to deliver the vaccine. As shown in FIG. 6, immunization with only two doses of as low as 25 μg of the vaccine via either intramuscular or intradermal routes was able to elicit high levels of S1-specific IgG. Specifically, two doses of intramuscular immunization with pSARS2-S were able to induce significant levels of S1-specific IgG in a dose-dependent fashion in BALB/c mice (FIGS. 6A and 6B), in which two doses of 50 μg and 100 μg administered by the needle-free system elicited IgG levels that are equivalent or higher (FIG. 6B) than that induced by three doses of 100 μg by needle injection (FIG. 2B). This was further confirmed by comparing S1-specific IgG in sera collected from BALB/c mice administered with two doses of 25 μg (FIG. 7A), 50 μg (FIG. 7B) and 100 μg (FIG. 7C) via either needle injection or needle-free system. Thus, needle-free administration of 50 μg and 100 μg induced significant levels of S1-specific IgG compared to needle injection in which all mice immunized with the needle-free system elicited S1-specific IgG compared to few from the group immunized using needle injection.

While intradermal needle injection of three doses of 100 μg failed to induce significant levels of specific IgG, two doses of pSARS2-S administered via the needle-free system induced significant levels of S1-specific IgG in a dose-dependent fashion (FIG. 6C and 6D). Importantly, the levels of S1-specific IgG were equivalent or higher than those generated by three doses administered by intramuscular needle injection. We further investigated the neutralizing activity of the sera from BALB/c mice immunized with two doses opSARS2-S using either needle injection or needle-free system. As shown in FIG. 8, two doses of needle-free immunization delivered intramuscularly were sufficient to induce high levels, reaching $1\times10^3$ of nAbs, that were statistically significant.

While the invention has been described in terms of its several exemplary embodiments, those skilled in the art will recognize that the invention can be practiced with modification within the spirit and scope of the appended claims. Accordingly, the present invention should not be limited to the embodiments as described above but should further include all modifications and equivalents thereof within the spirit and scope of the description provided herein.

This work was supported by King Abdulaziz City for Science and Technology (KACST), Riyadh, Saudi Arabia, through a research grant program (number 09-1), which is a part of the Targeted Research Program (TRP).

We claim:

1. A DNA vaccine able to induce an immune response against a SARS-CoV-2 coronavirus, comprising a DNA plasmid encoding a codon-optimized pSARS2 spike glycoprotein (pSARS2-S) as an immunogen from a SARS-CoV-2 coronavirus, wherein the pSARS2-S is codon-optimized for mammalian expression, and wherein the pSARS2-S N-terminal signal peptide is replaced with a signal peptide from a human IgG2 heavy chain.

2. The DNA vaccine of claim 1, wherein the DNA sequence encoding the codon-optimized pSARS2-S and encoding the signal peptide from the human IgG2 heavy chain has the nucleotide sequence of SEQ ID NO: 1.

3. The DNA vaccine of claim 1, wherein the DNA sequence of the signal peptide from the human IgG2 heavy chain encodes the amino acid sequence of SEQ ID NO:2.

4. The DNA vaccine of claim 1, wherein the DNA sequence encoding the signal peptide from the human IgG2 heavy chain has the nucleotide sequence of SEQ ID NO:3.

5. The DNA vaccine of claim 1, wherein the DNA sequence encodes a protein having the amino acid sequence of SEQ ID NO:4.

6. A DNA vaccine able to induce an immune response to a SARS-CoV-2 coronavirus comprising a DNA plasmid encoding the immunogen of SEQ ID NO: 1.

7. The DNA vaccine of claim 6, wherein the nucleotide sequence encodes a protein having the amino acid sequence of SEQ ID NO:4.

* * * * *

```
SEQUENCE LISTING

<160> NUMBER OF SEQ ID NOS: 4

<210> SEQ ID NO 1
<211> LENGTH: 3840
<212> TYPE: DNA
<213> ORGANISM: Artificial Sequence
<220> FEATURE:
<223> OTHER INFORMATION: Synthetic immunogen sequence

<400> SEQUENCE: 1
atgggatgga gctgtatcat cctcttcttg gtagcaacag ctacaggtgt ccactcccag      60
tgcgtgaatc tgactactcg gactcagctg cctcccgcct ataccaattc cttcacccgg     120
ggcgtgtact atcctgacaa ggtgtttaga agctccgtgc tgcactctac acaggatctg     180
tttctgccat tctttagcaa cgtgacctgg ttccacgcca tccacgtgag cggcaccaat     240
ggcacaaagc ggttcgacaa tcccgtgctg ccttttaacg atggcgtgta cttcgcctct     300
accgagaaga gcaacatcat cagaggctgg atctttggca ccacactgga ctccaagaca     360
cagtctctgc tgatcgtgaa caatgccacc aacgtggtca tcaaggtgtg cgagttccag     420
ttttgtaatg atcccttcct gggcgtgtac tatcacaaga acaataagag ctggatggag     480
tccgagttta gagtgtattc tagcgccaac aattgcacat ttgagtacgt gtcccagcct     540
ttcctgatgg acctggaggg caagcagggc aatttcaaga acctgaggga gttcgtgttt     600
aagaatatcg acggctactt caaaatctac agcaagcaca cccccatcaa cctggtgcgc     660
```

```
gacctgcctc agggcttcag cgccctggag cccctggtgg atctgcctat cggcatcaac    720
atcacccggt ttcagacact gctggccctg cacagaagct acctgacacc cggcgactcc    780
tctagcggat ggaccgcagg agctgccgcc tactatgtgg gctatctgca gccccggacc    840
ttcctgctga agtacaacga gaatggcacc atcacagacg cagtggattg cgccctggac    900
cccctgagcg agacaaagtg tacactgaag tcctttaccg tggagaaggg catctatcag    960
acatccaatt tcagggtgca gccaaccgag tctatcgtgc gctttcctaa tatcacaaac   1020
ctgtgcccat ttggcgaggt gttcaacgca accaggttcg ccagcgtgta cgcatggaat   1080
aggaagcgca tctctaactg cgtggccgac tatagcgtgc tgtacaactc cgcctctttc   1140
agcaccttta agtgctatgg cgtgtccccc acaaagctga atgacctgtg ctttaccaac   1200
gtgtacgccg attctttcgt gatcaggggc gacgaggtgc gccagatcgc acctggacag   1260
acaggcaaga tcgccgacta caattataag ctgccagacg atttcaccgg ctgcgtgatc   1320
gcctggaaca gcaacaatct ggattccaag gtcggcggca actacaatta tctgtaccgg   1380
ctgtttagaa agagcaatct gaagcccttc gagagggaca tctctacaga aatctaccag   1440
gccggcagca cccttgcaa tggcgtggag ggctttaact gttatttccc actgcagtcc   1500
tacggcttcc agcccacaaa cggcgtgggc tatcagcctt accgcgtggt ggtgctgagc   1560
tttgagctgc tgcacgcacc agcaacagtg tgcggcccca agaagtccac caatctggtg   1620
aagaacaagt gcgtgaactt caacttcaac ggcctgaccg gcacaggcgt gctgaccgag   1680
tccaacaaga agttcctgcc atttcagcag ttcggcaggg acatcgcaga taccacagac   1740
gccgtgcgcg acccacagac cctggagatc ctggacatca cccctgctc tttcggcggc   1800 gtgagcgtga tcacaccagg caccaataca agcaaccagg tggccgtgct gtatcaggac   1860
gtgaattgta ccgaggtgcc tgtggccatc cacgccgatc agctgacccc aacatggcgg   1920
gtgtacagca ccggctccaa cgtgttccag acaagagccg gatgcctgat cggagcagag   1980
cacgtgaaca attcctatga gtgcgacatc ccaatcggcg ccggcatctg tgcctcttac   2040
cagacccaga caaactctcc cagaagagcc cggagcgtgg cctcccagtc tatcatcgcc   2100
tataccatgt ccctgggcgc cgagaacagc gtggcctact ctaacaatag catcgccatc   2160
ccaaccaact tcacaatctc tgtgaccaca gagatcctgc ccgtgtccat gaccaagaca   2220
tctgtggact gcacaatgta tatctgtggc gattctaccg agtgcagcaa cctgctgctg   2280
cagtacggca gcttttgtac ccagctgaat agagccctga caggcatcgc cgtggagcag   2340
gataagaaca cacaggaggt gttcgcccag gtgaagcaaa tctacaagac cccccctatc   2400
aaggactttg gcggcttcaa ttttttccag atcctgcctg atccatccaa gccttctaag   2460
cggagcttta tcgaggacct gctgttcaac aaggtgaccc tggccgatgc cggcttcatc   2520
aagcagtatg gcgattgcct gggcgacatc gcagcccggg acctgatctg cgcccagaag   2580
tttaatggcc tgaccgtgct gccacccctg ctgacagatg agatgatcgc acagtacaca   2640
agcgccctgc tggccggcac catcacatcc ggatggacct tcggcgcagg agccgccctg   2700
cagatcccct ttgccatgca gatggcctat aggttcaacg gcatcggcgt gacccagaat   2760
gtgctgtacg agaaccagaa gctgatcgcc aatcagttta actccgccat cggcaagatc   2820
caggacagcc tgtcctctac agcctccgcc ctgggcaagc tgcaggatgt ggtgaatcag   2880
aacgcccagg ccctgaatac cctggtgaag cagctgagca gcaacttcgg cgccatctct   2940
agcgtgctga atgacatcct gagccggctg gacaaggtgg aggcagaggt gcagatcgac   3000
cggctgatca caggcagact gcagtctctg cagacctatg tgacacagca gctgatcagg   3060
```

```
gcagcagaga tcagggccag cgccaatctg gcagcaacca agatgtccga gtgcgtgctg      3120
ggccagtcta agagagtgga cttttgtggc aagggctatc acctgatgtc cttccctcag      3180
tctgccccac acggcgtggt gtttctgcac gtgacctacg tgcccgccca ggagaagaac      3240
ttcaccacag cccctgccat ctgccacgat ggcaaggccc actttccaag ggagggcgtg      3300
ttcgtgtcca acggcaccca ctggtttgtg acacagcgca atttctacga gccccagatc      3360
atcaccacag acaataccct tcgtgagcgg aactgtgacg tggtcatcgg catcgtgaac      3420
aataccgtgt atgatccact gcagcccgag ctggacagct ttaaggagga gctggataag      3480
tacttcaaga tcacacctc  ccctgacgtg gatctgggcg acatcagcgg catcaatgcc      3540
tccgtggtga acatccagaa ggagatcgac cgcctgaacg aggtggccaa gaatctgaac      3600
gagagcctga tcgacctgca ggagctgggc aagtatgagc agtacatcaa gtggccctgg      3660
tacatctggc tgggcttcat cgccggcctg atcgccatcg tgatggtgac catcatgctg      3720
tgctgtatga catcctgctg ttcttgcctg aagggctgct gtagctgtgg ctcctgctgt      3780
aaattcgatg aagatgactc cgagcccgtg ctgaaaggcg tgaaactgca ttacacttga      3840
```

<210> SEQ ID NO 2
<211> LENGTH: 19
<212> TYPE: PRT
<213> ORGANISM: human

<400> SEQUENCE: 2

Met Gly Trp Ser Cys Ile Ile Leu Phe Leu Val Ala Thr Ala Thr Gly
1               5                   10                  15

Val His Ser

<210> SEQ ID NO 3
<211> LENGTH: 57
<212> TYPE: DNA
<213> ORGANISM: human

<400> SEQUENCE: 3
atgggatgga gctgtatcat cctcttcttg gtagcaacag ctacaggtgt ccactcc      57

<210> SEQ ID NO 4
<211> LENGTH: 1279
<212> TYPE: PRT
<213> ORGANISM: Artificial Sequence
<220> FEATURE:
<223> OTHER INFORMATION: Synthetic immunogen sequence

<400> SEQUENCE: 4

Met Gly Trp Ser Cys Ile Ile Leu Phe Leu Val Ala Thr Ala Thr Gly
1               5                   10                  15

Val His Ser Gln Cys Val Asn Leu Thr Thr Arg Thr Gln Leu Pro Pro
            20                  25                  30

Ala Tyr Thr Asn Ser Phe Thr Arg Gly Val Tyr Tyr Pro Asp Lys Val
        35                  40                  45

Phe Arg Ser Ser Val Leu His Ser Thr Gln Asp Leu Phe Leu Pro Phe
    50                  55                  60

Phe Ser Asn Val Thr Trp Phe His Ala Ile His Val Ser Gly Thr Asn
65                  70                  75                  80

Gly Thr Lys Arg Phe Asp Asn Pro Val Leu Pro Phe Asn Asp Gly Val
                85                  90                  95

Tyr Phe Ala Ser Thr Glu Lys Ser Asn Ile Ile Arg Gly Trp Ile Phe
            100                 105                 110

```
Gly Thr Thr Leu Asp Ser Lys Thr Gln Ser Leu Leu Ile Val Asn Asn
            115                 120                 125

Ala Thr Asn Val Val Ile Lys Val Cys Glu Phe Gln Phe Cys Asn Asp
        130                 135                 140

Pro Phe Leu Gly Val Tyr Tyr His Lys Asn Asn Lys Ser Trp Met Glu
145                 150                 155                 160

Ser Glu Phe Arg Val Tyr Ser Ser Ala Asn Asn Cys Thr Phe Glu Tyr
                165                 170                 175

Val Ser Gln Pro Phe Leu Met Asp Leu Glu Gly Lys Gln Gly Asn Phe
            180                 185                 190

Lys Asn Leu Arg Glu Phe Val Phe Lys Asn Ile Asp Gly Tyr Phe Lys
        195                 200                 205

Ile Tyr Ser Lys His Thr Pro Ile Asn Leu Val Arg Asp Leu Pro Gln
210                 215                 220

Gly Phe Ser Ala Leu Glu Pro Leu Val Asp Leu Pro Ile Gly Ile Asn
225                 230                 235                 240

Ile Thr Arg Phe Gln Thr Leu Leu Ala Leu His Arg Ser Tyr Leu Thr
                245                 250                 255

Pro Gly Asp Ser Ser Ser Gly Trp Thr Ala Gly Ala Ala Ala Tyr Tyr
            260                 265                 270

Val Gly Tyr Leu Gln Pro Arg Thr Phe Leu Leu Lys Tyr Asn Glu Asn
        275                 280                 285

Gly Thr Ile Thr Asp Ala Val Asp Cys Ala Leu Asp Pro Leu Ser Glu
290                 295                 300

Thr Lys Cys Thr Leu Lys Ser Phe Thr Val Glu Lys Gly Ile Tyr Gln
305                 310                 315                 320

Thr Ser Asn Phe Arg Val Gln Pro Thr Glu Ser Ile Val Arg Phe Pro
                325                 330                 335

Asn Ile Thr Asn Leu Cys Pro Phe Gly Glu Val Phe Asn Ala Thr Arg
            340                 345                 350

Phe Ala Ser Val Tyr Ala Trp Asn Arg Lys Arg Ile Ser Asn Cys Val
        355                 360                 365

Ala Asp Tyr Ser Val Leu Tyr Asn Ser Ala Ser Phe Ser Thr Phe Lys
370                 375                 380

Cys Tyr Gly Val Ser Pro Thr Lys Leu Asn Asp Leu Cys Phe Thr Asn
385                 390                 395                 400

Val Tyr Ala Asp Ser Phe Val Ile Arg Gly Asp Glu Val Arg Gln Ile
                405                 410                 415

Ala Pro Gly Gln Thr Gly Lys Ile Ala Asp Tyr Asn Tyr Lys Leu Pro
            420                 425                 430

Asp Asp Phe Thr Gly Cys Val Ile Ala Trp Asn Ser Asn Asn Leu Asp
        435                 440                 445

Ser Lys Val Gly Gly Asn Tyr Asn Tyr Leu Tyr Arg Leu Phe Arg Lys
450                 455                 460

Ser Asn Leu Lys Pro Phe Glu Arg Asp Ile Ser Thr Glu Ile Tyr Gln
465                 470                 475                 480

Ala Gly Ser Thr Pro Cys Asn Gly Val Glu Gly Phe Asn Cys Tyr Phe
                485                 490                 495

Pro Leu Gln Ser Tyr Gly Phe Gln Pro Thr Asn Gly Val Gly Tyr Gln
            500                 505                 510

Pro Tyr Arg Val Val Val Leu Ser Phe Glu Leu Leu His Ala Pro Ala
        515                 520                 525
```

-continued

Thr Val Cys Gly Pro Lys Lys Ser Thr Asn Leu Val Lys Asn Lys Cys
530                535                540

Val Asn Phe Asn Phe Asn Gly Leu Thr Gly Thr Gly Val Leu Thr Glu
545                550                555                560

Ser Asn Lys Lys Phe Leu Pro Phe Gln Gln Phe Gly Arg Asp Ile Ala
        565                570                575

Asp Thr Thr Asp Ala Val Arg Asp Pro Gln Thr Leu Glu Ile Leu Asp
        580                585                590

Ile Thr Pro Cys Ser Phe Gly Gly Val Ser Val Ile Thr Pro Gly Thr
        595                600                605

Asn Thr Ser Asn Gln Val Ala Val Leu Tyr Gln Asp Val Asn Cys Thr
610                615                620

Glu Val Pro Val Ala Ile His Ala Asp Gln Leu Thr Pro Thr Trp Arg
625                630                635                640

Val Tyr Ser Thr Gly Ser Asn Val Phe Gln Thr Arg Ala Gly Cys Leu
                645                650                655

Ile Gly Ala Glu His Val Asn Asn Ser Tyr Glu Cys Asp Ile Pro Ile
                660                665                670

Gly Ala Gly Ile Cys Ala Ser Tyr Gln Thr Gln Thr Asn Ser Pro Arg
        675                680                685

Arg Ala Arg Ser Val Ala Ser Gln Ser Ile Ile Ala Tyr Thr Met Ser
690                695                700

Leu Gly Ala Glu Asn Ser Val Ala Tyr Ser Asn Asn Ser Ile Ala Ile
705                710                715                720

Pro Thr Asn Phe Thr Ile Ser Val Thr Thr Glu Ile Leu Pro Val Ser
                725                730                735

Met Thr Lys Thr Ser Val Asp Cys Thr Met Tyr Ile Cys Gly Asp Ser
                740                745                750

Thr Glu Cys Ser Asn Leu Leu Leu Gln Tyr Gly Ser Phe Cys Thr Gln
        755                760                765

Leu Asn Arg Ala Leu Thr Gly Ile Ala Val Glu Gln Asp Lys Asn Thr
770                775                780

Gln Glu Val Phe Ala Gln Val Lys Gln Ile Tyr Lys Thr Pro Pro Ile
785                790                795                800

Lys Asp Phe Gly Gly Phe Asn Phe Ser Gln Ile Leu Pro Asp Pro Ser
                805                810                815

Lys Pro Ser Lys Arg Ser Phe Ile Glu Asp Leu Leu Phe Asn Lys Val
        820                825                830

Thr Leu Ala Asp Ala Gly Phe Ile Lys Gln Tyr Gly Asp Cys Leu Gly
        835                840                845

Asp Ile Ala Ala Arg Asp Leu Ile Cys Ala Gln Lys Phe Asn Gly Leu
850                855                860

Thr Val Leu Pro Pro Leu Leu Thr Asp Glu Met Ile Ala Gln Tyr Thr
865                870                875                880

Ser Ala Leu Leu Ala Gly Thr Ile Thr Ser Gly Trp Thr Phe Gly Ala
                885                890                895

Gly Ala Ala Leu Gln Ile Pro Phe Ala Met Gln Met Ala Tyr Arg Phe
        900                905                910

Asn Gly Ile Gly Val Thr Gln Asn Val Leu Tyr Glu Asn Gln Lys Leu
        915                920                925

Ile Ala Asn Gln Phe Asn Ser Ala Ile Gly Lys Ile Gln Asp Ser Leu
930                935                940

```
Ser Ser Thr Ala Ser Ala Leu Gly Lys Leu Gln Asp Val Val Asn Gln
945                 950                 955                 960

Asn Ala Gln Ala Leu Asn Thr Leu Val Lys Gln Leu Ser Ser Asn Phe
                965                 970                 975

Gly Ala Ile Ser Ser Val Leu Asn Asp Ile Leu Ser Arg Leu Asp Lys
            980                 985                 990

Val Glu Ala Glu Val Gln Ile Asp Arg Leu Ile Thr Gly Arg Leu Gln
        995                 1000                1005

Ser Leu Gln Thr Tyr Val Thr Gln Gln Leu Ile Arg Ala Ala Glu
    1010                1015                1020

Ile Arg Ala Ser Ala Asn Leu Ala Ala Thr Lys Met Ser Glu Cys
    1025                1030                1035

Val Leu Gly Gln Ser Lys Arg Val Asp Phe Cys Gly Lys Gly Tyr
    1040                1045                1050

His Leu Met Ser Phe Pro Gln Ser Ala Pro His Gly Val Val Phe
    1055                1060                1065

Leu His Val Thr Tyr Val Pro Ala Gln Glu Lys Asn Phe Thr Thr
    1070                1075                1080

Ala Pro Ala Ile Cys His Asp Gly Lys Ala His Phe Pro Arg Glu
    1085                1090                1095

Gly Val Phe Val Ser Asn Gly Thr His Trp Phe Val Thr Gln Arg
    1100                1105                1110

Asn Phe Tyr Glu Pro Gln Ile Ile Thr Thr Asp Asn Thr Phe Val
    1115                1120                1125

Ser Gly Asn Cys Asp Val Val Ile Gly Ile Val Asn Asn Thr Val
    1130                1135                1140

Tyr Asp Pro Leu Gln Pro Glu Leu Asp Ser Phe Lys Glu Glu Leu
    1145                1150                1155

Asp Lys Tyr Phe Lys Asn His Thr Ser Pro Asp Val Asp Leu Gly
    1160                1165                1170

Asp Ile Ser Gly Ile Asn Ala Ser Val Val Asn Ile Gln Lys Glu
    1175                1180                1185

Ile Asp Arg Leu Asn Glu Val Ala Lys Asn Leu Asn Glu Ser Leu
    1190                1195                1200

Ile Asp Leu Gln Glu Leu Gly Lys Tyr Glu Gln Tyr Ile Lys Trp
    1205                1210                1215

Pro Trp Tyr Ile Trp Leu Gly Phe Ile Ala Gly Leu Ile Ala Ile
    1220                1225                1230

Val Met Val Thr Ile Met Leu Cys Cys Met Thr Ser Cys Cys Ser
    1235                1240                1245

Cys Leu Lys Gly Cys Cys Ser Cys Gly Ser Cys Cys Lys Phe Asp
    1250                1255                1260

Glu Asp Asp Ser Glu Pro Val Leu Lys Gly Val Lys Leu His Tyr
    1265                1270                1275

Thr
```